United States Patent [19]

Blye et al.

[11] 4,252,800
[45] Feb. 24, 1981

[54] 7α-METHYLNORETHINDRONE ENANTHATE AND ITS USE IN LONG TERM SUPPRESSION OF FERTILITY IN FEMALE MAMMALS

[75] Inventors: Richard Blye, Highland; Hyun K. Kim, Bethesda, both of Md.

[73] Assignee: United States of America, Washington, D.C.

[21] Appl. No.: 82,056

[22] Filed: Oct. 5, 1979

[51] Int. Cl.³ ............................................. A61K 31/56
[52] U.S. Cl. ................................... 424/243; 260/397.4
[58] Field of Search ............................. 424/238, 243; 260/397.4

[56] References Cited

U.S. PATENT DOCUMENTS 3,341,557   9/1967   Babcock et al. ................ 260/397.45

OTHER PUBLICATIONS

Gould et al. "Journ. Amer. Chem. Soc." vol. 79 (1957) pp. 4472-4475.
Duncan et al., "Proc. of the Soc. for Exp. Biol. Med.", vol. 116, p. 800 (1964).
Pharriss, "Contraception", vol. 1, No. 2 (1970) p. 25.

*Primary Examiner*—Elbert L. Roberts
*Attorney, Agent, or Firm*—Holman & Stern

[57] ABSTRACT

A novel steroid, 7α-methylnorethindrone enanthate, having utility in prolonged suppression of fertility in female mammals, and methods for the use of the compound are claimed.

7 Claims, No Drawings

7α-METHYLNORETHINDRONE ENANTHATE AND ITS USE IN LONG TERM SUPPRESSION OF FERTILITY IN FEMALE MAMMALS

BACKGROUND OF THE INVENTION

The ability of the female sex steroids, namely estrogens and progesterone, to inhibit fertility in mammals has been known for many years. The primary mechanism involved is the inhibition of ovulation although many other steps in the reproductive process are vulnerable to alterations in the normal circulating patterns of these hormones. Inhibition of ovulation derives from the effect of the sex steroids on the hypothalamic-hypophyseal axis where they may inhibit synthesis and/or release of gonadotrophin releasing factors (LHRH) and/or the gonadotrophins (luteinizing hormone-LH, follicle stimulating hormone-FSH) themselves.

The natural sex hormones are seldom used to control fertility in mammals including man because of their weak oral activity which necessitates a daily injection schedule. Not until the development of potent orally active estrogens and progestational agents did this method of fertility control assume commercial significance.

Combination oral contraceptives are the most commonly used method for the hormonal suppression of fertility. These drugs contain small quantities of a synthetic estrogen and progestogen and are taken daily for twenty or twenty-one days of each menstrual cycle. While cycle control is usually excellent with these preparations, a host of side effects, some of them serious, have been associated with their use. Progestin-only contraceptives lack many of the side effects of the combination pills but are less effective in preventing pregnancy as well as in producing regular menstrual cycles. Long-acting synthetic progestational agents are effective for several months following a single intramuscular injection but are also associated with abnormal bleeding episodes or, in some cases, the absence of bleeding altogether (amenorrhea). Thus the greatest drawback of the currently available long-acting progestational agents in the control of fertility is their induction of a broad spectrum of aberrant bleeding problems. These bleeding problems may be controlled to some extent by the administration of estrogens at periodic intervals in the treatment cycle.

For many years researchers have sought a compound which is both progestational and estrogenic in nature with the hope that this single drug entity would be not only efficacious in controlling fertility but permit control of uterine bleeding. Such a compound would obviate the need for additional estrogen to control bleeding problems.

Norethindrone (17α-ethynyl-19-nortestosterone) was one of the first synthetic progestational agents to be incorporated into oral contraceptive tablets. In combination with ethynylestradiol or ethynylestradiol-3-methyl ether (mestranol), norethindrone has become one of the most widely used and accepted oral contraceptives in the world. It has long been known that esterification of the 17-hydroxyl group with long chain fatty acids yields compounds with prolonged hormonal activity. The heptanoate ester of norethindrone (norethindrone enanthate) is a long-acting progestational agent and contraceptive but its use has been associated with abnormal bleeding problems characteristic of progestogen-only contraceptive methods. 7α-Methylation of norethindrone confers substantial estrogenic activity on the parent molecule. 7α-Methylnorethindrone enanthate exhibits both progestational and estrogenic activity and has been shown to interfere with certain reproductive processes in experimental animals for extended periods of time.

DESCRIPTION OF THE PRIOR ART

U.S. Pat. No. 3,341,557 to Babcock, et al. discloses tha the compound 7α-methyl-17α-ethynyl-19-nortestosterone (7α-methylnorethindrone) possesses greater activity as an anti-fertility agent, but lower activity as a progestational agent than the closely related known compound 17α-ethynyl-19-nortestosterone (norethindrone). G. W. Duncan, et al., in an article appearing in *Proceedings of the Society for Experimental Biological Medicine* 116, No. 800 (1964), disclose a substantial increase of oral gonadotropin inhibiting, pregnancy inhibiting and uterotropic potencies for 7α-methylnorethindrone as compared to norethindrone. B. B. Pharriss, et al. in an article appearing in *Contraception* 1, 87 (1970) disclose the estrogenic and progestational properties of 7α-methylnorethindrone and, in particular, point out that the compound prevented conception in rats at 100 micrograns per day, orally, and 50 micrograms per day, systemically. Of particular note is their observation that even at 1 and 5 times the effective anti-fertility dose in rats, fertility was re-established within 8 to 12 days after terminating continuous dosing for 14 to 28 days. None of these disclosures, however, report long lasting suspension of fertility from single or even multiple anti-fertility effective doses of either compound.

SUMMARY OF THE INVENTION

Accordingly, it is a primary object of the invention to provide a compound which has progestational and inherent estrogenic characteristics and significantly prolonged anti-fertility effects in female mammals.

Still another object of the invention is to provide methods for long-lastingly suppressing fertility in a female mammal using the compound in accordance with the first object of the invention.

The above and other objects are achieved in accordance with the present invention by providing a novel steroid, namely, 7α-methylnorethindrone enanthate which is useful as an anti-fertility agent when administered to female mammals. In addition to having progestational and estrogenic characteristics, the compound suppresses fertility for prolonged periods following a single injection.

DESCRIPTION OF THE PREFERRED EMBODIMENTS

The disclosed invention is the steroid 7α-methylnorethindrone enanthate and methods of its use for prolonged anti-fertility in female mammals. The compound's structural formula is

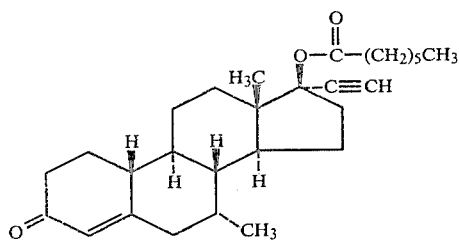

Its systematic name is 7α-methyl-17β-hydroxy-17α-ethynylestr-4-en-3-one 17β-heptanoate.

In general the compound is parenterally administered i.e., subcutaneously or intramuscularly in a pharmaceutically acceptable carrier. For compounds of this type pharmaceutically acceptable carriers include oily substances such as sesame oil, arachis oil, peanut oil, olive oil and castor oil.

Experiments in rats comparing 7α-methylnorethindrone enanthate to norethindrone enanthate, another anti-fertility steroid effective in human females at a dose of 200 mg administered every 2 or 3 months, indicate that 7α-methylnorethindrone enanthate is at least 5 times more effective than norethindrone enanthate in suppressing fertility as measured by suppression of cornification of the vaginal endometrium and estrous cycles.

Based on these experiments, it is anticipated that 7α-methylnorethindrone enanthate may be effectively used in human females in a dose range of from about 40 mg to about 100 mg at an interval of from about 2 months to about 6 months. Optimum dose in this range is one which is effective to control fertility as well as uterine bleeding.

7α-Methylnorethindrone enanthate may be synthesized by a number of different routes. The detailed schemes of synthesis are disclosed in the examples described below.

The following examples will serve to disclose the synthesis of the compound and the practice of the invention, but are not to be considered as limiting:

A. SYNTHESIS OF THE COMPOUND

EXAMPLE 1

7α-Methylnorethindrone enanthate was esterified by reacting 7α-methylnorethindrone with a freshly distilled heptanoyl chloride in the presence of a base such as pyridine.

EXAMPLE 2

The second procedure involved the reaction of the thallium salt of 7α-methylnorthindrone with heptanoyl chloride. The steroidal alcohol (500 mg, 1.6 mM) and thallous ethoxide (480 mg, 1.92 mM) were dissolved in dry benzene (50 ml). The solvent was slowly distilled while being continuously replaced with fresh benzene. When approximately 50 ml of benzene was distilled, the reaction mixture was cooled and treated dropwise with heptanoyl chloride (380 mg, 2.6 mM). The reaction was completed by heating the mixture at reflux for 3.5 hours. The colored reaction mixture was filtered and washed twice with water, pH 7 buffer, water and brine. The aqueous washes were extracted twice with ethyl acetate. The combined organic extracts were dried over sodium sulfate and evaporated in vacuo to yield a crude product. However, thin layer chromatography developed in ether: hexane (8:2) showed mainly one product. Purification by dry column chromatography gave a viscous oil, 547 mg (81% yield). IR(KBr):$\nu_{max}$ 1745, 1675, and 1620 cm$^{-1}$. Nmr (CDCl$_3$, 90 L MHz) δ0.80 (d, J=7 Hz, 3 H, C-7α-CH$_3$), 0.89 (t, J=4.5 Hz, 3 H terminal CH$_3$), 0.93 (s, 3 H, C-18 CH$_3$), 2.60 (s, 1 H CCH), and 5.88 (s, 1 H, C-4 H) ppsm. Analysis calculated for C$_{28}$H$_{40}$O$_3$, C, 79.20; H, 9.50 Found: C, 78.90; H, 9.80.

EXAMPLE 3

In a third procedure, a concomitant ethynylation and esterification were employed as shown below:

Reduction of 3-methoxy-7α-methylestra-1,3,5(10)-trien-17-one

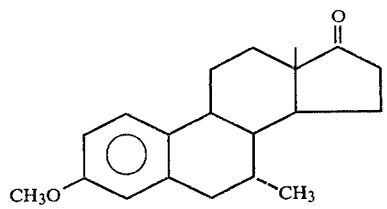

by sodium borohydride, and Birch reduction of the resulting alcohol by sodium in liquid ammonia followed by conversion of 1,4-dihydro compound to the corresponding ethylene ketal and oxidation using Collins reagent gave the following intermediate:

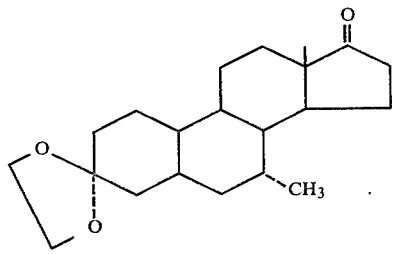

Ethynylation of this ketone was accomplished by the action of lithium acetylide-ethylenediamine complex in dimethyl sulfoxide. The crude ethynyl compound was hydrolyzed with dilute hydrochloric acid to a crystalline enone which was esterified by heptanoic anhydride to yield the desired 17β-enanthate.

B. METHOD FOR USE OF THE COMPOUND

EXAMPLE 4

In an experiment designed to demonstrate suppression of estrus, 20 mg. of the compound was dissolved in sesame oil and administered as a single subcutaneous injection to each of 10 female rats. Ten other animals were treated in the same manner using norethindrone enanthate and 10 control animals were injected with the vehicle alone. Estrus suppression was determined by daily vaginal smears of the test animals, starting the day of treatment and continuing for 90 days. The duration for which cornification was suppressed equals the number of days between a treatment and the first cornified smear minus 2. A cyclicity index was determined by dividing the total 4 or 5 day cycles observed by the maximum number of 4-day cycles expected after return of cornification, multiplied by 100. The results of this experiment are found in Table I.

From Table I it will readily be seen that the subject compound suppressed vaginal cornification of the test animals for a mean of 60 days plus or minus 9.66 days, while norethindrone enanthate resulted in only a 12 day plus or minus 4.56 day suppression. Control animals exhibited estrus in 1.2 days plus or minus 0.33 days. Of those animals showing at least 1 cornified smear after the treatment, with or without cycles, the 7α-methylnorethindrone enanthate treated group has a cyclicity index after first cornification of 5.89 plus or minus 3.83 cycles; by contrast the norethindrone enanthate treated group had a cyclicity index of 27.08 plus or minus 8.21 cycles and the controls had a cyclicity index of 80.13 plus or minus 7.02 cycles. Of particular interest is the fact that 4 out of 10 of the 7α-methylnorethindrone enanthate treated group failed to show any cornification throughout the 90 day observation period after treatment. Of the other six animals treated with the subject compound, two showed only questionable cyclicity.

EXAMPLE 5

In an experiment comparing the estrous suppressing activity of a range of doses of 7α-methylnorethindrone enanthate, norethindrone enanthate, and medroxyprogesterone acetate (Depo-Provera T.M. of Upjohn), 4, 8 or 16 mg of the compound in sesame oil or, in the case of Depo-Provera, in an aqueous solution, was administered subcutaneously to 10 animals at each dose level. Ten control animals were injected with sesame oil alone. Estrus suppression was determined by the same criteria as in Example 4 above, i.e., by cornification suppression and cyclicity index. The results of this experiment are found in Table II.

From the table it will be readily seen that even at the low dose of 4 mg, the subject compound has potent estrus-suppressing activity. Perhaps as significant is the low cyclicity index of the subject compound at each of the dose levels studied, as shown by Table III.

EXAMPLE 6

At the end of the experiment summarized in Example 5 above, the animals were sacrificed at an expected day of estrus or any day if the animals were not cycling. The oviducts were flushed and the ovaries weighed. The data are summarized in Table IV.

As can be readily seen in the table, animals treated with the subject compound had significantly lower ovarian weights than those treated with the other compounds at every dose level, and an almost three-fold reduction in the number of total eggs recovered from the oviducts of the animals at sacrifice. From these data it can readily be seen that the subject compound not only suppresses the estrous cycle but also significantly reduces the number of ova shed even at periods in excess of 90 days from the time of treatment.

TABLE I

Estrus Suppression in Rats by a Single Subcutaneous Dose of 7α-Methylnorethindrone Enanthate or Norethindrone Enanthate

| Compound | Dose mg | N | Animals showing no Cornification throughout the Observation Period after Treatment | Animals showing at least one Cornfield Smear after the Treatment, with or without Cycles | | |
|---|---|---|---|---|---|---|
| | | | | Number of Animals | Duration for which Cornification was Suppressed Mean ± SE (days) | Cyclicity Index after first Cornification Mean ± SE (%) |
| Vehicle | — | 10 | 0 | 10 | 1.20 ± 0.33 | 80.13 ± 7.02 |
| Norethindrone Enanthate | 20.0 | 10 | 0 | 10 | 12.00 ± 4.56 | 27.08 ± 8.21 |
| 7α-Methylnorethindrone Enanathate | 20.0 | 10 | 4 | 6 | 60.00 ± 9.66 | 5.89 ± 3.83 |

TABLE II

Estrus Suppression: Comparison of 7α-Methylnorethindrone Enanthate, Depo-Provera TM and Norethindrone Enanthate

| Compound | Dose mg | N | Animals showing no Cornification throughout the Observation Period after Treatment | Animals showing at least one Cornified Smear after the Treatment, with or without Cycles | | |
|---|---|---|---|---|---|---|
| | | | | Number of Animals | Duration for which Cornification was Suppressed Mean ± SE (days) | Cyclicity Index after first Cornification Mean ± SE (%) |
| Vehicle | 0 | 10 | 0 | 10 | 2.2 ± 0.7 | 92.3 ± 1.9 |
| Depo-Provera TM | 4 | 10 | 0 | 10 | 30.6 ± 2.0 | 84.8 ± 4.5 |
| Norethindrone Enanthate | 4 | 10 | 0 | 10 | 5.0 ± 1.0 | 85.2 ± 2.8 |
| 7α-Methylnorethindrone Enanthate | 4 | 10 | 0 | 10 | 30.5 ± 7.7 | 9.6 ± 4.5 |
| Depo-Provera TM | 8 | 10 | 1 | 9 | 54.4 ± 4.2 | 66.3 ± 8.9 |
| Norethindrone Enanthate | 8 | 10 | 0 | 10 | 6.9 ± 3.6 | 79.3 ± 5.7 |
| 7α-Methylnorethindrone Enanthate | 8 | 10 | 3 | 7 | 30.9 ± 8.5 | 20.3 ± 7.1 |
| Depo-Provera TM | 16 | 10 | 5 | 5 | 71.2 ± 9.0 | 26.1 ± 14.9 |
| Norethindrone Enanthate 7α-Methylnorethindrone | 16 | 10 | 0 | 10 | 19.8 ± 2.9 | 52.6 ± 7.9 |

TABLE II-continued

Estrus Suppression:
Comparison of 7α-Methylnorethindrone Enanthate,
Depo-Provera TM and Norethindrone Enanthate

| Compound | Dose mg | N | Animals showing no Cornification throughout the Observation Period after Treatment | Animals showing at least one Cornified Smear after the Treatment, with or without Cycles | | |
|---|---|---|---|---|---|---|
| | | | | Number of Animals | Duration for which Cornification was Suppressed Mean ± SE (days) | Cyclicity Index after first Cornification Mean ± SE (%) |
| Enanthate | 16 | 10 | 4 | 6 | 48.2 ± 12.0 | 15.1 ± 6.4 |

TABLE III

Estrus Suppression by Various Doses of Depo-Provera, TM Norethindrone Enanthate and 7α-Methylnorethindrone Enanthate: Resumption of Estrus Cycles

| CDB- | Dose mg | N | Number of Animals showing one or more Cornified Smears | Duration of Estrus Suppression Mean ± SE (days) | No. of Animals Exhibiting cycles (at the end of experiment) | | | Time for return of regular cycles Mean ± SE (days) |
|---|---|---|---|---|---|---|---|---|
| | | | | | Normal | Questionable | None | |
| Vehicle | — | 10 | 10 | 2.2 ± 0.7 | 10 | 0 | 0 | 2.2 ± 0.7 |
| | 4.0 | 10 | 10 | 30.6 ± 2.0 | 10 | 0 | 0 | 31.5 ± 2.2 |
| *Depo- | 8.0 | 10 | 9 | 54.4 ÷ 4.2 | 8 | 0 | 2 | 53.1 ± 3.8** |
| Provera TM | 16.0 | 10 | 5 | 71.2 ± 9.0 | 1 | 1 | 8 | ++ |
| Norethin- | 4.0 | 10 | 10 | 5.0 ± 1.0 | 10 | 0 | 0 | 7.3 ± 2.2 |
| drone | 8.0 | 10 | 10 | 6.9 ± 3.6 | 8 | 2 | 0 | 9.2 ± 4.0 |
| Enanthate | 16.0 | 10 | 10 | 19.8 ± 2.9 | 6 | 2 | 2 | 24.0 ± 3.3 |
| 7α-Methyl- | | | | | | | | |
| norethin- | 4.0 | 10 | 10 | 30.5 ± 7.7 | 0 | 3 | 7 | + |
| norethin- | 8.0 | 10 | 7 | 30.9 ± 8.5 | 1 | 1 | 8 | ++ |
| drone Ethanate | 16.0 | 10 | 6 | 48.2 ± 12.0 | 1 | 0 | 9 | ++ |

*In aqueous suspension
**N = 8
+No animals established regular cycles.
++Only one animal established regular cycles.

TABLE IV

Influence of a Single Subcutaneous Injection of Depo-provera TM, Norethindrone Enanthate and 7α-Methylnorethindrone Enanthate On Ovarian Weights and Ovulation over 90 Days Later

| CDB- | Dose | N | FBW(g) Mean ± SE | No. of Animals with eggs in oviducts | Total eggs recovered | Ovarian weight (mg) | Mean ± SE |
|---|---|---|---|---|---|---|---|
| Vehicle | — | 10 | 320 ± 12 | 9 | 116 | 99.8 | ±3.9 |
| *Depo-Provera TM | 4.0 | 10 | 341 ± 11 | 10 | 164 | 101.0 | ±5.0 |
| | 8.0 | 10 | 359 ± 11 | 9 | 139 | 99.2 | ±6.0 |
| | 16.0 | 10 | 375 ± 17 | 2 | 28 | 83.0 | ±4.3 |
| Norethindrone | 4.0 | 10 | 300 ± 7 | 9 | 127 | 91.5 | ±5.8 |
| Enanthate | 8.0 | 10 | 311 ± 8 | 8 | 116 | 91.7 | ±6.1 |
| | 16.0 | 10 | 301 ± 7 | 9 | 119 | 83.9 | ±7.1 |
| 7α-Methylnor- | 4.0 | 10 | 259 ± 4 | 3 | 37 | 49.4 | ±5.4 |
| ethindrone | 3.0 | 10 | 278 ± 6 | 3 | 34 | 51.6 | ±9.2 |
| Enanthate | 16.0 | 10 | 266 ± 5 | 1 | 12 | 35.3 | ±4.3 |

*In aqueous suspension

The embodiments of the invention in which an exclusive property or privilege is claimed are defined as follows:

1. A method of inducing long term suppresssion of fertility in a female mammal comprising administering an anti-fertility-effective amount of 7α-methylnorethindrone enanthate to said female mammal.

2. The method of claim 1 wherein said administration is in a parenteral dose.

3. The method of claim 2 wherein said parenteral dose is a single dose.

4. The method of claim 1 wherein said female mammal is a human female.

5. The method of claim 4 wherein said administration is in a single parenteral dose.

6. The method of claim 4 wherein said administration is at a frequency of from about once every 2 months to about once every 6 months.

7. The method of claim 4 or 6 wherein said dose is in a range from about 40 mg to about 200 mg.

* * * * *

UNITED STATES PATENT AND TRADEMARK OFFICE
CERTIFICATE OF CORRECTION

PATENT NO. : 4,252,800                                          Page 1 of 2
DATED      : February 24, 1981
INVENTOR(S): Richard Blye et al.

It is certified that error appears in the above—identified patent and that said Letters Patent is hereby corrected as shown below:

Column 3, line 46, should read -- 7$\alpha$-Methylnorethindrone was esterified by --

Column 4, line 3, should read -- 1675, and 1620 cm$^{-1}$. Nmr (CDCl$_3$, 90 MH$_z$) $\delta$ 0.80 --

Column 4, line 6, should read -- CCH), and 5.88 (s, 1 H, C-4 H) ppm. Analysis calcu- --

Column 4, lines 31-42, the diagram should be:

UNITED STATES PATENT AND TRADEMARK OFFICE
CERTIFICATE OF CORRECTION

PATENT NO. : 4,252,800  
DATED : February 24, 1981  
INVENTOR(S) : Richard Blye et al.

Page 2 of 2

It is certified that error appears in the above—identified patent and that said Letters Patent is hereby corrected as shown below:

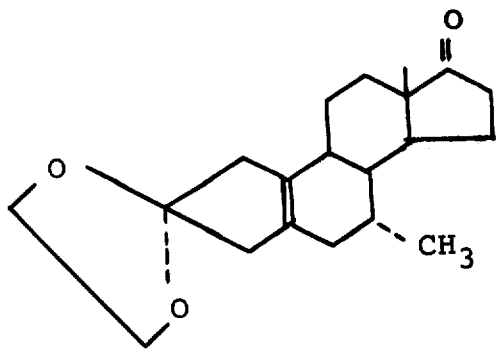

Signed and Sealed this

Eighth Day of September 1981

[SEAL]

Attest:

GERALD J. MOSSINGHOFF

Attesting Officer     Commissioner of Patents and Trademarks